(12) United States Patent
Perrault et al.

(10) Patent No.: US 6,169,094 B1
(45) Date of Patent: Jan. 2, 2001

(54) COMPOSITIONS OF (S) (-)-AMISULPRIDE

(75) Inventors: Ghislaine Perrault, Paris; Hans Schoemaker, Gif sur Yvette; Joël Miget, Mousseaux sur Seine, all of (FR)

(73) Assignee: Sanofi-Synthelabo, Paris (FR)

( * ) Notice: Under 35 U.S.C. 154(b), the term of this patent shall be extended for 0 days.

(21) Appl. No.: 09/114,900

(22) Filed: Jul. 14, 1998

(51) Int. Cl.⁷ .......................... A61K 9/20; C07D 207/08
(52) U.S. Cl. ......................... 514/310; 424/451; 548/567
(58) Field of Search ........................... 548/567; 424/451, 424/464; 514/980

(56) References Cited

U.S. PATENT DOCUMENTS

| | | | |
|---|---|---|---|
| 4,401,822 | * | 8/1983 | Thominet et al. .................... 548/567 |
| 5,407,823 | * | 4/1995 | Sokoloff et al. .................. 435/252.3 |
| 5,719,197 | * | 2/1998 | Kanios et al. ........................ 514/781 |

FOREIGN PATENT DOCUMENTS

WO 98/11881   3/1998   (WO) .

OTHER PUBLICATIONS

Schoemaker et al. "Neurochemical Characteristics of Amisulpride, an Atypical Dopamine $D_2/D_3$ Receptor Antagonist with both Presynaptic and Limbic Selectivity" The Journal of Pharmacology and Experimental Therapeutics, vol. 280, No. 1, pp. 83–97, 1997.*

Perrault et al., "Psychopharmacological Profile of Amisulpride: An Antipsychotic Drug with presynaptic $D_2/D3$ Dopamine Receptor Antagonist Activity and Limbic Selectivity", The Journal of Pharmacology and Experimental Therapeutics, vol. 280, No. 1, pp. 73–82, 1997.*

* cited by examiner

Primary Examiner—F. T. Moezie
(74) Attorney, Agent, or Firm—Foley & Lardner

(57) ABSTRACT

A composition is provided comprising an antipsychotic effective amount of (S)(−)-amisulpride, (S)-(−)-4-amino-N-[(1-ethylpyrrolidin-2-yl)methyl]-5-ethylsulfonyl)-2-methoxybenzamide. A preferred composition comprises the (D)-tartrate salt of (S)(−)-amisulpride. The (S)(−) enantiomer exhibits antipsychotic properties and administration of the specific enantiomer reduces adverse side effects by reducing toxicity.

2 Claims, No Drawings

COMPOSITIONS OF (S) (-)-AMISULPRIDE

BACKGROUND OF THE INVENTION

This invention relates to a novel composition containing optically pure (S)(−)-amisulpride or a pharmaceutically acceptable salt thereof.

This composition possesses antipsychotic properties useful in the treatment of positive, negative, affective or cognitive symptoms of schizophrenia, dysthymia, autism, tardive dyskinesia induced by neuroleptics, Tourette disease (tics), manic or depressive symptoms in patients with bipolar disorders, sudden attacks of delirium, migraine and drug addiction while inducing therapeutic effects at doses lower and with a higher safety ratio than the racemic mixture of amisulpride or its salts.

This invention also relates to a method of treatment utilizing this composition in the therapeutical indications described above.

Amisulpride, belonging to the benzamide series, is described in U.S. Pat. No. 4,401,822 to Thominet et al. Amisulpride is known for its antiapomorphine activity. Chemically, the (S)(−) isomer is (S)-(−)-4-amino-N-[(1-ethylpyrrolidin-2-yl)methyl]-5-(ethylsulfonyl)-2-methoxybenzamide, referred thereafter as (S)(−)-amisulpride.

At the present time, amisulpride is available only as a racemic mixture, hereinafter called (R,S)-amisulpride. (R,S)-Amisulpride is mainly used in the treatment of acute and chronic schizophrenic disorders, in which positive symptoms (such as delusions, hallucinations, thought disorders) and/or negative symptoms (such as blunted affect, emotional and social withdrawal) are prominent. More particularly (R,S)-amisulpride is used for treating patients having predominant primary negative symptoms. (R,S)-Amisulpride is also used in the treatment of depressive disorders such as dysthimia.

Pharmacological profile of (R,S)-amisulpride is well described in H. Schoemaker et al., *The Journal of Pharmacology and Experimental Therapeutics*, 280 (1997), 83–97 and Gh. Perrault et al., *The Journal of Pharmacology and Experimental Therapeutics*, 280 (1997), 73–82. In particular, it is reported how this pharmacological profile is distinct from that of classical neuroleptics such as haloperidol and from that of another benzamide, remoxipride. It is characterizd by a preferential blockade of $D_2$ and $D_3$ receptors with presynaptic and limbic selectivity.

According to these properties (R,S)-amisulpride has certain advantages over other antipsychotics (neuroleptic agents). (R,S)-amisulpride shows a clinical efficacy against negative, positive, affective or cognitive symptoms of schizophrenia, a low propensity to produce extrapyramidal side effects and a good general tolerance.

SUMMARY OF THE INVENTION

It has been now discovered that the (S)(−) enantiomer of amisulpride, of formula:

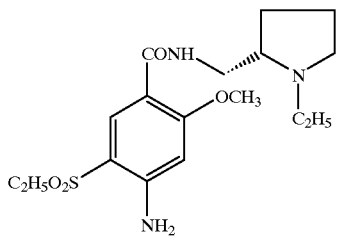

or pharmaceutically salts thereof are effective antipsychotic agents with a qualitatively similar pharmacological profile, while inducing therapeutical effect at lower doses and showing a higher safety ratio than (R,S)-amisulpride. Novel compositions containing optically pure (S)(−)-amisulpride or any acceptable salt thereof, which have antipsychotic activity while inducing therapeutic effect at lower doses and showing a higher safety ratio than (R,S)-amisulpride are also disclosed.

Also included within the present invention are novel compositions containing optically pure (S)(−) enantiomer of amisulpride or any acceptable salt thereof, which are useful in the treatment of negative, positive, affective and cognitive symptoms of schizophrenic disorders, dysthymia, autism, tardive dyskinesia induced by neuroleptics, Tourette disease, manic or depressive symptoms, migraine headaches, sudden attacks of delirium, but also in weaning drug addicts.

DETAILED DESCRIPTION OF THE INVENTION

The present invention encompasses a method of treatment capable of eliciting antipsychotic properties, which comprises administering to a patient suffering from psychotic disorders and/or depressive disorders, an amount of (S)(−)-amisulpride or a pharmaceutically salt thereof, substantially free of its (R)(+)-stereoisomer, sufficient to alleviate schizophrenic symptoms while allowing to avoid or strongly reduce risks of appearance of side effects associated with (R,S)-amisulpride.

The present invention also emcompasses a composition adapted for the treatment of a patient in need of antipsychotic and/or antidepressive therapy, containing (S)(−)-amisulpride or a pharmaceutically salt thereof, substantially free of its (R)(+)-stereoisomer, which have antipsychotic activity while allowing to avoid or strongly reduce risks of appearance of side effects associated with the racemic mixture of (R,S)-amisulpride.

Pure (S)(−)-amisulpride shows an increased therapeutic potency as compared to the racemic mixture that could have been expected for an active enantiomer of a racemic mixture. In addition, after ingestion of the same dose of (S)(−)-amisulpride or (R,S)-amisulpride, occurrence of side effects is comparable. Therefore, the safety ratio of (S)(−)-amisulpride is markedly increased as compared to the racemic mixture.

As a result, a composition according to the invention allows the dose of active substance to be reduced by about 2-fold in comparison with the traditional dosage of the racemic mixture, while side effects can be markedly reduced.

As used in the present application, the term "substantially free of the (R)(+) stereoisomer" means that the composition contains at least 90% by weight of (S)(−)-amisulpride and 10% by weight or less of (R)(+)-amisulpride. In the most preferred embodiment the term "substantially free of the (R)(+) stereoisomer" means that the composition contains at least 99% by weight of (S)(−)-amisulpride and 1% by weight or less of (R)(+)-amisulpride.

The term "eliciting antipsychotic properties" means relief from the symptoms associated with psychotic disorders and/or depressive disorders, which include but is not limited to schizophrenia and dysthimia.

The term "side effect" as used in the present application includes but is not limited to extrapyramidal side effects.

The term "pharmaceutically acceptable salt" refers to salts prepared from pharmaceutically acceptable non-toxic acids including inorganic acids and organic acids. Among acids may be mentioned inclusively but not in a limiting manner, inorganic or organic acids such as hydrochloric, hydrobromic, sulphuric, phosphoric, oxalic, acetic, tartaric, citric, or methane sulphonic acid. Especially preferred among these acids are the tartaric acids and particularly the [S- (R*,R*) ]-2, 3-dihydroxybutanedioic acid (Chemical abstract registry number : 147-71-7), hereinafter called D-(−)-tartaric acid.

The preferred salt of (S)(−)-amisulpride is the D-(−)-tartrate of (S)(−)-amisulpride.

The synthesis of the (S)(−)-amisulpride can be performed by the following method:

2-methoxy-4-amino-5-mercaptobenzoic acid is treated with ethylsulfate to provide the 5-ethylthiobenzoic acid which is then oxidized to provide the 2-methoxy-4-amino-5-ethylsulphonyl benzoic acid. This acid is then reacted with (S)-(−)-1-ethyl-2-aminomethylpyrrolidine. This reaction is carried out by activating either the acid moiety or the amino moiety by means known in the art.

Thus the acid moiety may be converted into the corresponding acyl halide, alkyl ester, reactive ester, aryl ester, N-hydroxyimide ester of a carbonic acid or a haloformic ester, azide, hydrazide, azolide, acid isothiocyanate, trichloroacetophenone, or triphenylphophine derivative. Alternatively, the acid moiety is left intact and the amine activated by reaction with phosphorus chloride, phosphorus oxychloride, a dialkyldiaryl-, or orthophenylenechlorophosphite, an alkyl- or aryldichlorophosphite, or the formation of an isothiocyanate of the amine or a substituted urea or sulphamide.

The activated compound is then reacted with the unactivated component by means well-known in the art.

In a further embodiment the free acid and the free amine may be reacted together in the presence of a condensing agent such as, for example, silicon tetrachloride, trichlorophenylsilane, phosphoric anhydride, a carbodiimide or an alkoxyacetylene.

In yet another embodiment of this synthetic procedure there is provided the (S)(−) enantiomer of a dihaloalkylamine of the formula:

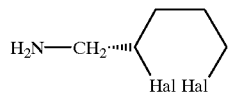

this dihaloalkylamine is then reacted with 2-methoxy-4-amino-5-ethylsulfonyl benzoic acid as above to provide a compound of the formula:

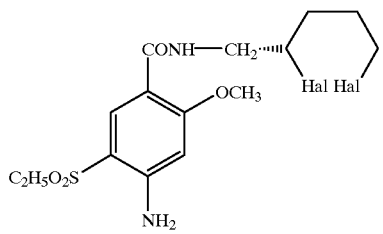

It is then reacted with ethylamine to produce the (S)(−)-amisulpride. Salts can then be prepared by action of corresponding acids.

(S)(−)-Amisulpride and its pharmaceutically acceptable salts are used in form of capsules, tablets, pills, in granular form for oral administration or as an injectable solution; the preparation of these is known per se. It is possible to use substances which are inert relative to (S)(−)-amisulpride and its pharmaceutically acceptable salts of the invention. Among these are the vehicles customarily used in medicinal preparations, such as sugars, starch and starch derivatives, calcium phosphate, calcium carbonate, lubricants such as magnesium stearate, disintegrants such as sodium carboxymethylcellulose, croslinked carboxymethylcelluloses and crospovidone, which are well known to one skilled in the art, and which are described in the Handbook of Pharmaceutical Excipients (Ed. Ainley Wade and Paul J. Weller, *American Pharmaceutical Association*, Washington, 1994).

In the case where an oral composition is used, a suitable dosage range for use is, e.g., from about 20 mg to about 250 mg of (S)(−)-amisulpride per day.

The invention is further defined by reference to the following examples describing in detail the preparation of the (S)(−)-amisulpride and salts thereof, the therapeutical potency of (S)(−)-amisulpride in comparison with the racemic mixture and the preparation of a tablet containing the (S)(−)-amisulpride.

EXAMPLES

4.1. Example 1

Preparation of D-(−)-tartrate of (S)-(−)-4-amino-N-[(1-ethylpyrrolidin-2-yl)methyl]-5-(ethylsulfonyl)-2-methoxybenzamide 2-methoxy-4-amino-5-ethylthiobenzoic acid 159 g of 2-methoxy-4-amino-5-mercaptobenzoic acid, 355 cm³ of water and 160 cm³ of 30% sodium hydroxyde solution are placed in a flask fitted with a condenser. The mixture is heated until the solid dissolves, then 123 g of ethylsulfate is added. The mixture is heated to reflux, treated with 10 cm³ of 30% sodium hydroxyde solution, then heated to reflux for 1 hour. After cooling, 800 cm³ of water is added and the solution is filtered. The precipitate obtained by adding 100 cm³ of concentrated hydrochloric acid in the presence of ether is drained, washed with water and dried.

162 g of 2-methoxy-4-amino-5-ethylthio benzoic acid is obtained (yield=88%).

2-methoxy-4-amino-5-ethylsulphonylbenzoic acid 123 g of 2-methoxy-4-amino-5-ethylthiobenzoic acid is dissolved in 542 cm³ of hot acetic acid. The solution obtained is cooled to 35° C., then 185 cm³ of 131 vol hydrogen peroxide is added in small quantities while the temperature is raised to 80° C.

The temperature is lowered to 40° C. and the mixture is kept at this temperature for some hours then cooled to 10°

C. The precipitate formed is drained, washed with acetic acid and dried, then dissolved in 600 cm$^3$ of water and 100 cm$^3$ of 20% ammonia. The precipitate formed by adding 70 cm$^3$ of concentrated hydrochloric acid is cooled, drained, washed with water and dried.

61,5 g of 2-methoxy-4-amino-5-ethylsulphonylbenzoic acid hydrate is obtained (yield=42%); Melting point: 95–100° C.

(S)-(−)-4-amino-N-[(1-ethylpyrrolidin-2-yl)methyl]-5-(ethylsulfonyl)-2-methoxybenzamide 95 g of 2-methoxy-4-amino-5-ethylsulphonylbenzoic acid dissolved in 370 ml of acetone, in the presence of 37 g of trielthylamine, is treated with 40 g of ethyl chloroformate with 57 g of (S)-(−)-1-ethyl-2-aminomethylpyrrolidine. 115 g of (S)-(−)-N-(1-ethyl-2-pyrrolidinylmethyl)- 2-methoxy-4-amino-5-ethylsulphonylbenzamide is obtained (yield=84%).

D-(−)-tartrate of (S)-(−)-4-amino-N-[(1-ethylpyrrolidin-2-yl)methyl]-5-(ethylsulfonyl)-2-methoxybenzamide 133 g of (S)-(−)-4-amino-N-[(1-ethylpyrrolidin-2-yl) methyl ]-5-(ethylsulfonyl)-2-methoxybenzamide is dissolved in 500 ml of methanol, then 54 g of D-(−)-tartaric acid dissolved in 80 ml of methanol is added. The crystals formed after seeding are drained, washed with methanol then dried.

After re-crystallisation in methanol, 106 g of D-(−)-tartrate of (S)-(−)-4-amino-N-[(1-ethylpyrrolidin-2-yl) methyl]-5-(ethylsulfonyl)-2-methoxybenzamide is obtained.

(yield=56%); Melting point: 98–108° C.; $[\alpha]_D^{20}$=+7,5° (c=0.05, water); ee>98%.

4.2. Example 2
Affinity for limbic $D_2$ dopamine receptors

This study was carried out to compare affinity of (S)(−)-amisulpride and (R,S)-amisulpride for $D_2$ receptors in the limbic system and striatum of the rat in vivo. It is now widely believed that blockade by neuroleptics of $D_2$ receptors in the limbic system is related to their antipsychotic properties whereas blockade of $D_2$ receptors in the striatum (extrapyramidal system) reflects their propensity to induce extrapyramidal side effects. We therefore compared the ability of (S)(−)-amisulpride and (R,S)-amisulpride to displace the binding of $^3$H-raclopride (a ligand which recognizes $D_2$ receptors) in both regions in the rat brain.

The basic methodology for this study is described in Schoemaker et al (The Journal of Pharmacology and Experimental Therapeutics, 280 (1997), 83–97). Briefly, the radioligand (9 μCi/200 μl) was injected into the tail vein of Male Sprague-Dawley rats 45 min before sacrifice. Test drug or vehicle was administered in a final volume of 1 ml 75 min before $^3$H-raclopride. Brain structures (striatum, limbic system and cerebellum) were dissected by hand and the incorporated radioactivity was measured after overnight digestion in 0.5 ml of Soluene. The radioactivity incorporated into the cerebellum was taken as nonspecific binding.

| Brain structure | Displacement of $^3$H-raclopride binding ($ED_{50}$ mg/kg, ip) | |
|---|---|---|
| | (S) (−)-amisulpride | (R,S)-amisulpride |
| Limbic areas | 4.3 | 17.3 |
| Striatum | 24.5 | 43.6 |
| Selectivity ratio limbic vs striatum | 5.7 | 2.5 |

(S)(−)-amisulpride was 4-fold more potent than (R,S)-amisulpride at displacing $^3$H-raclopride from limbic $D_2$ receptors and about 2-fold more potent than (R,S)-amisulpride to displace the radioligand from striatal $D_2$ receptors. In these conditions, the selectivity of (S)(−)-amisulpride for limbic vs striatal $D_2$ receptors was about 2-fold higher than for (R,S)-amisulpride, suggesting that the former compound should exhibit a better separation between extrapyramidal side effects and antipsychotic activity (higher safety index).

The potency of (S)(−)- and (R,S)-amisulpride in tests predictive of antipsychotic activity and side effects were compared.

4.3. Example 3
Activity in tests predictive of antipsychotic activity.

This study was carried out to compare the potency of (S)(−)-amisulpride and (R,S)-amisulpride in tests considered to be predictive of antipsychotic activity, namely antagonism of hypermotility, induced in the rat by amphetamine or apomorphine injected 30 min after drug treatment.

Apomorphine-induced hyperactivity was recorded for 15 min in individual photocell activity cages, 15 min after administration of apomorphine (0.25 mg/kg, sc) to rats previously placed in the activity cages for a 30 min habituation period. These experimental conditions produce low baseline locomotor activity suitable for assessing increases in locomotion produced by apomorphine.

d-Amphetamine-induced hyperactivity was recorded for 20 min, 30 min after injection of d-amphetamine (2 mg/kg, ip) immediately after placing rats in the activity cages without habituation according to Gh. Perrault et al (Journal of Pharmacology and Experimental Therapeutics 280 (1997) 73–82).

| | $ED_{50}$ mg/kg, ip | |
|---|---|---|
| Test | (S) (−)-amisulpride | (R,S)-amisulpride |
| Antagonism of d-amphetamine-induced hypermotility | 1.2 | 3 |
| Antagonism of apomorphine- induced hypermotility | 15 | 30 |

(S)(−)-Amisulpride was 2–3 fold more potent than (R,S)-amisulpride at blocking apomorphine or amphetamine-induced hypermotility in the rat, two models predictive of efficacy on positive symptoms of schizophrenia. This result is in line with the higher relative affinity of (S)(−)-amisulpride than (R,S)-amisulpride for limbic $D_2$ receptors in vivo and is expected for an active enantiomer of a racemate compound.

4.4. Example 4
Activity in tests predictive of centrally mediated side effects This study was carried out to compare the relative ability of (S)(−)-amisulpride and (R,S)-amisulpride to induce centrally mediated side effects, e.g. extrapyramidal and sedative effects in the rat. The propensity of the drugs to induce extrapyramidal side effects was assessed by measuring their potential to induce catalepsy and to antagonize apomorphine-induced stereotyped behaviour and the sedative potential of the drugs was evaluated by their capacity to decrease spontaneous locomotor activity in the rat.

Stereotypies induced by apomorphine (0.5 mg/kg, sc) were observed every 10 min for 30 min immediately after apomorphine injected 30 min after drug treatment in rats placed in individual Plexiglas cages (25×20×14 cm high). For scoring stereotypies, the following scale was used: 0: asleep; 1: awake; quiet; 2: locomotion, head bobbing; 3: sniffing; 4: licking; 5: chewing/gnawing. For each rat, a global score was calculated by averaging the 3 stereotypy scores obtained at 10 min intervals.

Spontaneous locomotor activity was measured for 20 min immediately after rats were placed in the activity cages, 30 min after drug treatment.

The occurrence of catalepsy in rats was assessed using the four-cork test. This measurement was performed by placing each paw of the rat on a 2.5 cm high cork (diameter 1.2 cm). Distance between contralateral corks was 8 cm and between ipsilateral corks 13 cm. Catalepsy time was measured for a maximum of 2 min at 2 hours, and 4 hours after ip drug treatment.

| | $ED_{50}$ mg/kg, ip | |
|---|---|---|
| Test | (S) (-)-amisulpride | (R,S)-amisulpride |
| Antagonism of apomorphine-induced stereotypies | 100 | 115 |
| Induction of catalepsy | >100 | >100 |
| Decrease in spontaneous locomotor activity | 100 | 100 |

| Safety ratios | | |
|---|---|---|
| Catalepsy/d-amphetamine hypermotility | >83 | >33 |
| Apomorphine stereotypies/ d-amphetamine hypermotility | 6.6 | 3.8 |
| Decrease in locomotion/ d-amphetamine hypermotility | 83 | 33 |

As shown in the table, both compounds decreased locomotor activity with a similar potency ($ED_{50}$=100 mg/kg). Moreover, (S)(-)-amisulpride and (R,S)-amisulpride were equipotent at antagonizing apomorphine-induced stereotypies. Finally, neither compound induced catalepsy at doses up to 100 mg/kg, ip. When the ratio between the doses inducing catalepsy or antagonizing apomorphine-induced stereotypies (predictive of the occurrence of extrapyramidal side effects in man) and those blocking amphetamine-induced hypermotility (predictive of antipsychotic activity) are compared, (S)(-)-amisulpride shows a higher safety ratio (~2-times) than (R,S)-amisulpride. Similarly, when the ratio between doses that cause decrease in locomotor activity (predictive of the occurrence of sedation in man) and those blocking amphetamine-induced hypermotility (predictive of antipsychotic activity are compared, (S)(-)-amisulpride exhibits a higher safety ratio (~2.5) than (R,S)-amisulpride.

In conclusion, these results show that (S)(-)-amisulpride displays a pharmacological profile qualitatively similar to that of (R,S)-amisulpride. However, (S)(-)-amisulpride appears twice as potent as (R,S)-amisulpride in tests predictive of antipsychotic activity (antagonism of apomorphine or amphetamine hyperlocomotion) as would be expected for an active enantiomer of a racemic mixture. Therefore, lower doses of (S)(-)-amisulpride than (R,S)-amisulpride would be expected to produce antipsychotic effects in schizophrenic patients.

However, unexpectedly in models predictive of the occurrence of extrapyramidal and sedative side effects, the potency of both compounds is quite similar. As (S)(-)-amisulpride is twice as potent as (R,S)-amisulpride in tests predictive of antipsychotic activity, this results in a higher safety ratio (2 to 2.5-fold) for (S)(-)-amisulpride as compared to (R,S)-amisulpride. Accordingly, (S)(-)-amisulpride might produce antipsychotic activity in schizophrenic patients with a higher safety ratio with respect to extrapyramidal and sedative side effects than (R,S)-amisulpride.

4.5. Example 5

Oral tablet formulation containing 25 mg of (S)(-)-amisulpride (as amisulpride base).

| | % (by weight) | Unit mass (mg) |
|---|---|---|
| (S) (-)-amisulpride D(-)-tartrate | 20.0 | 35 |
| lactose 150 mesh | 51.8 | 90.65 |
| hydroxypropylmethylcellulose Pharmacoat 606 | 3.0 | 5.25 |
| microcrystaline cellulose Avicel PH1O1 | 20.0 | 35 |
| Primojel | 4.0 | 7 |
| Colloidal silica | 0.2 | 0.35 |
| Magnesium stearate | 1.0 | 1.75 |

(S)(-)-Amisulpride D-(-)-tartrate and all other components except colloidal silica and magnesium stearate are mixed in a mixer granulator (Lodige), 8% water and granulate are added for 1–3 min. The obtained mixture is dryed in an oven at 55° C., and calibrated through a 0.8 mm sieve, then lubricated, adding the magnesium stearate and Aerosil, in a turbula mixer for 10 min. Tablet is produced to a unit mass of 175 mg.

What is claimed is:

1. A dosage composition which comprises an antipsychotic effective amount of (S)-(-)-4-amino-N-[(1-ethylpyrrolidin-2-yl)methyl]-5-ethylsulfonyl)-2-methoxybenzamide, ((S)(-)-amisulpride), or a pharmaceutically acceptable salt thereof, substantially free of its (R)-(+)-stereoisomer, and pharmaceutically acceptable excipients.

2. The dosage composition of claim 1, wherein said salt of (S) (-)-amisulpride is the D-(-)-tartrate salt.

* * * * *